United States Patent [19]

Myers et al.

[11] Patent Number: 4,977,156

[45] Date of Patent: Dec. 11, 1990

[54] AMINO PIPERAZINE ESTERS SHOWING BIOCIDAL ACTIVITY

[75] Inventors: Jimmy Myers, Sweeny; Wilfred W. Wilson, Freeport, both of Tex.

[73] Assignee: The Dow Chemical Company, Midland, Mich.

[21] Appl. No.: 224,597

[22] Filed: Jul. 26, 1988

[51] Int. Cl.$^5$ .................. A61K 31/495; C07D 295/92
[52] U.S. Cl. ..................... 514/255; 544/389; 544/400
[58] Field of Search ................. 544/389, 400; 514/255

[56] References Cited

U.S. PATENT DOCUMENTS

| | | | |
|---|---|---|---|
| 2,436,685 | 2/1948 | Baltzly et al. | 544/386 |
| 2,472,496 | 6/1949 | Stewart | 544/386 |
| 2,535,971 | 12/1950 | Turner | 544/389 |
| 2,617,803 | 11/1952 | Turner | 544/389 |
| 2,794,804 | 6/1957 | Kushner et al. | 544/402 |
| 2,861,072 | 11/1958 | Weston et al. | 544/392 |
| 2,943,090 | 6/1960 | Semb et al. | 544/401 |
| 2,945,860 | 7/1960 | Schmidt-Barbo et al. | 544/389 |
| 3,015,657 | 1/1962 | Geschickter et al. | 544/389 |
| 3,015,659 | 1/1962 | Rorig | 544/389 |
| 3,142,679 | 7/1964 | Barrett et al. | 544/363 |
| 3,198,799 | 8/1965 | Regnier et al. | 544/389 |
| 3,213,097 | 10/1965 | Forbes et al. | 544/389 |
| 3,230,223 | 1/1966 | Baget et al. | 544/363 |
| 3,251,761 | 5/1966 | Holtschmidt et al. | 544/410 |
| 3,274,054 | 9/1966 | Tomcufcik et al. | 544/389 |
| 3,331,830 | 7/1967 | Tomcufcik et al. | 544/386 |
| 3,331,842 | 7/1967 | Delalande | 544/389 |
| 3,793,322 | 2/1974 | Shroff et al. | 544/386 |
| 3,847,922 | 11/1974 | Ost et al. | 544/389 |
| 4,112,091 | 9/1978 | Nesvadba | 544/389 |
| 4,247,549 | 1/1981 | Ohnmacht et al. | 544/389 |

OTHER PUBLICATIONS

Makromol Chem. 177, 2259–2269 (1976) Uber Einige Copolyurethane Ausgehend von Piperazin.

*Primary Examiner*—Cecilia Shen
*Attorney, Agent, or Firm*—Carol J. Cavender; Barbara J. Sutherland

[57] ABSTRACT

Amino piperazine esters, preferably of the formula:

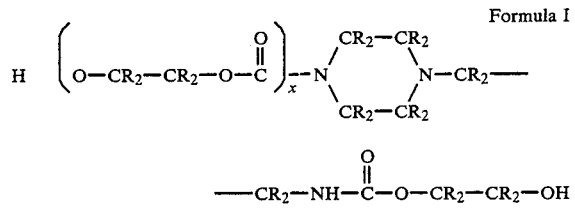

Formula I wherein x is 0 or 1 and each R is independently hydrogen or inert substitution, are produced by reacting an (optionally substituted) N-(2-aminoethyl) piperazine with an (optionally substituted) alkylene carbonate. The novel compounds are biocides that retard the growth of fungi and are also useful in preparing polymers.

9 Claims, No Drawings

AMINO PIPERAZINE ESTERS SHOWING BIOCIDAL ACTIVITY

TECHNICAL FIELD

The present invention relates to the field of piperazine compounds and, more particularly, to substituted piperazine derivatives and their use as biocides and in polymers.

BACKGROUND OF THE INVENTION

Fungi cause damage to crops and structures amenable to fungal growth, such as wood structures and the like. Having a wide variety of fungicides available to combat fungal damage is generally advantageous. When fungi develop immunity to known types of fungicides, use of different fungicides is indicated. Also, different types of fungicides find application in different environments.

Accordingly, it is desirable to have a novel family of fungicides. It is especially desirable to have a family of fungicides which retain activity when incorporated into polymers. Such fungicides are especially useful in environments in which smaller molecules would be removed, for instance, by contact with water or solvents.

SUMMARY OF THE INVENTION

In one aspect the invention is a compound selected from the group represented by the formula:

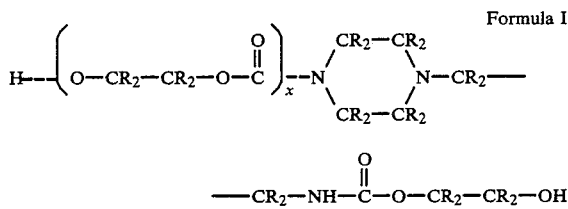

Formula I wherein x is 1 or 0 and each R is independently hydrogen or inert substitution.

In another aspect, the invention is a process comprising the steps of reacting an N-(2-aminoethyl) piperazine compound with an alkylene carbonate.

In yet another aspect, the invention is a method of retarding or eliminating the growth of a fungus in an environment that is conducive to the growth of the fungus, comprising placing in the environment a compound having a structure corresponding to Formula I in an amount effective to retard growth of a fungus.

New compounds or compositions of matter produced by interacting N-(2-aminoethyl) piperazines with alkylene carbonates are disclosed. The new compounds have biocidal properties and may be used, for instance, to retard or eliminate the formation or growth of fungi. The compounds are also useful in forming polymers by reaction of the hydroxyl and/or amine functionality with a polyfunctional compound reactive therewith, for instance, a polyepoxide, a polycarboxylic acid anhydride or halide, an polyisocyanate or the like.

DETAILED DESCRIPTION OF THE INVENTION

The compounds of the invention are referred to herein as amino piperazine esters and are preferably 4-[2-(2-hydroxy-1-alkoxycarboxyamino)alkyl]-1-piperazine-carboxylic acid, 1,2-alkanediol monoesters. Preferably the amino piperazine esters correspond to the following formula:

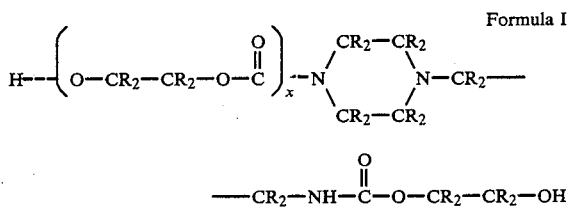

Formula I wherein x is 0 or 1 and each R independently is hydrogen or inert substitution, that is, substitution which does not interfere substantially with the biocidal action of the amino piperazine ester. Inert substitution includes such groups as alkyl, alkoxy, phenoxy and benzyloxy groups; chlorine, fluorine, bromine, iodine and nitro groups and the like; and is preferably alkyl, alkoxy, phenoxy, benzyloxy groups or chlorine. The alkyl, cycloalkyl, alkoxy, phenoxy, benzyloxy groups and the like are unsubstituted or inertly substituted, preferably by at least one halogen, more preferably chlorine. Alkyl, cycloalkyl and alkoxy groups preferably have from about 1 to about 20 carbons, more preferably from about 1 to about 8 carbon atoms and, most preferably, from about 1 to about 4 carbon atoms. Phenoxy and benzyloxy groups preferably have from about 6 to about 15, more preferably from about 6 to about 12, and most preferably from about 6 to about 10 carbon atoms. Suitable halogens are chlorine, fluorine, bromine and iodine. Each R is most preferably H. When all of the R groups are H, and x is 1, the compound is 4-[2-(2-hydroxy-1-ethoxycarboxyamino)ethyl]-1-piperazine-carboxylic acid, 1,2-ethanediol monoester. The molecular weight of the compound is 305. In ambient temperature, the compound is solid and has a melting point within the range of about 69° to 74° C.

The new compounds are suitably produced by reacting unsubstituted or inertly substituted N-(2-aminoethyl) piperazines with alkylene carbonates, which alkylene carbonates are unsubstituted or inertly substituted. The reaction is schematically represented by the following sequence:

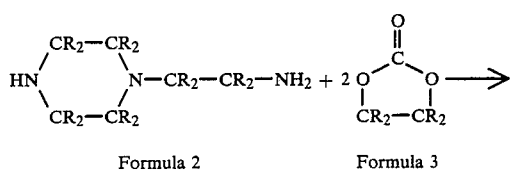

Formula 2                Formula 3

-continued

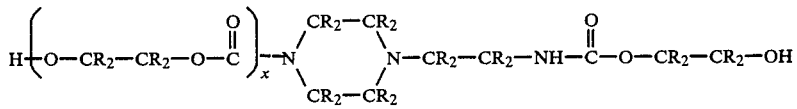

Formula 1

In this invention, the mole ratio of alkylene carbonate to N-(2-aminoethyl) piperazine compound ranges from about 0.5 to about 10, preferably from about 1.7 to about 2.3, most preferably from about 1.9 to about 2.1 moles of alkylene carbonate to 1 mole of N-(2-aminoethyl) piperazine compound.

When between about 1 and about 2 moles of 1,2-alkylene carbonate are reacted with a mole of an N-(2-aminoethyl)piperazine compound, mixtures of product compounds where x is 0 and 1 are generally produced. Because an alkylene carbonate compound generally reacts preferentially with the primary aliphatic amine of the N-(2-aminoethyl) piperazine compound rather than with the secondary amine ring nitrogen, the mixture of product compounds generally corresponds to compounds represented by Formula 1 wherein x is 1 and other compounds of Formula 1 wherein x is 0. Therefore, compounds of the invention correspond to those wherein x is 0 or 1.

All alkylene carbonates reactive with primary amines and a secondary amine ring nitrogen such as are present in an N-(2-aminoethyl) piperazine compound are suitable for use in the practice of the invention. Preferably, the alkylene carbonates are ones represented by Formula 3 wherein each R is independently hydrogen, a halogen, an unsubstituted or inertly substituted alkyl group, preferably of from about one to about 6 carbon atoms, an unsubstituted or inertly substituted alkoxy group, preferably of from about one to about 6 carbon atoms, an unsubstituted or inertly substituted aryl group, preferably of from about 6 to about 12 carbon atoms or an unsubstituted or inertly substituted aryloxy group, preferably of from about 6 to about 12 carbon atoms. More preferably, each R is independently hydrogen, a halogen, a methoxy group, a chlorine-substituted methoxy group, a methyl group or a chlorine-substituted methyl group, an ethoxy group, a chlorine-substituted ethoxy group, a ethyl group or a chlorine-substituted ethyl group, a methyl group substituted by an alkoxy group of from about 1 to about 4 carbon atoms or by an aryloxy group of from about 6 to about 10 carbon atoms, a phenoxy group, a chlorine-substituted phenoxy group, a phenoxy group substituted by an alkyl or alkoxy group of from about 1 to about 4 carbon atoms, a phenyl group or a chlorine-substituted phenyl group or a phenyl substituted by an alkyl or alkoxy group of from about 1 to about 4 carbon atoms. Suitable halogens include chlorine, bromine, iodine, and fluorine and are preferably chlorine or fluorine, more preferably chlorine. Inert substituents are described hereinabove. Chlorine substitution includes one, two or three chlorine groups attached to each carbon atom in a group.

The alkylene carbonates most preferred for use in the practice of the invention include ethylene carbonate, butylene carbonate, 1-chloroethylene carbonate, propylene carbonate, 3,3,3-trichloro-1,2-propylene carbonate, 3-tertiary butoxy-1,2-propylene carbonate, 3-(4-(tertiary butyl)phenoxy)-1,2-propylene carbonate, 3-(2-chloro-4-(tertiary butyl)phenoxy)-1,2-propylene carbonate, 3-(3-chloro-4-(tertiary butyl)phenoxy)-1,2-propylene carbonate, 3-(3,5-dichloro-4-(tertiary butyl)-phenoxy)-1,2-propylene carbonate, 3-(2,6-dichloro-4-(tertiary butyl)phenoxy-1,2-propylene carbonate and 3-(4-(nonachloro-tertiary butyl)phenoxy)-1,2-propylene carbonate.

N-(2-aminoethyl) piperazine compounds suitable for use in the practice of the invention are all N-(2-aminoethyl) piperazine compounds reactive with such alkylene carbonates. Preferably the N-(2-aminoethyl) piperazine compounds are those represented by Formula 2 wherein each R group is independently hydrogen or inert substitution as described for the product amino piperazine esters. N-(2-aminoethyl) piperazine compounds most preferred for use in the practice of the invention include N-(2-aminoethyl) piperazine, N-(2-aminoethyl) octachloropiperazine, N-(2-aminoethyl)-2-trichloromethyl piperazine, N-(2-aminotetrachloroethyl) piperazine, N-(2-amino-2-chloroethyl)piperazine and the like.

A reaction between an alkylene carbonate and an N-(2-amino) piperazine compound is generally exothermic, and is preferably carried out in the liquid phase under atmospheric or near atmospheric pressure. The temperature of the reaction is preferably high enough to maintain the reactants in liquid phase and to maintain a convenient reaction rate. Accordingly, the temperature generally suitably ranges from about 25° C. to about 200° C. For convenience, the reaction pressure is preferably about atmospheric pressure or slightly higher, e.g. less than about 2 atmospheres.

The reaction may be carried in either a batch or a continuous mode. In either mode, the interaction of the reactants is preferably controlled to prevent overheating from the exothermic reaction.

The new products are biocides and have the ability to retard or to eliminate growth of fungi in environments suitable for formation and growth of such fungi. Examples of such environments include gardens, wherein plants, such as squash, melons, grapes, roses and the like, are grown; house siding or roofs and other similar well known environments in which fungi thrive. Aspergillus niger is exemplary of fungi whose growth that can be retarded by the compounds of the present invention.

The amino piperazine esters of the invention are used in amounts sufficient to retard growth of fungi, preferably in amounts sufficient to kill the fungi. The amounts suitably used vary from application to application. For instance, in a garden environment suitable concentrations for application are generally in the range of from about 0.25 to about 10, preferably from about 0.5 to about 5, more preferably from about 0.5 to about 3 weight percent fungicide in a solvent or dispersing liquid such as water.

Amino piperazine esters of the invention are also suitably used in the preparation of polymers. The compounds wherein x is 1 are monomers having two hydroxyl groups suitable for reaction with polyfunctional compounds having groups reactive therewith. Exemplary of such groups are carboxylic acid anhydrides, carboxylic acid halides such as acyl chlorides, isocyanates, epoxy groups and other reactive heterocyclic groups and the like. When x is 0, the compounds of the invention have one such reactive hydroxyl group and additionally have a secondary ring amine. The amine is suitable for reaction with polyfunctional compounds having groups reactive therewith. Exemplary of such groups are the groups listed above which are reactive with a hydroxyl group as well as groups reactive with amine groups including carboxylic acids and the like. Polymers incorporating the amino piperazine esters of the invention preferably have molecular weights in excess of about 1200, preferably 15,000, more preferably 30,000. Amino piperazine esters preferably become bound into a polymer chain as repeating units therein. These repeating units preferably alternate with repeating units of at least one other monomer copolymerized with the amino piperazine ester. When the amino piperazines esters become bound into a polymer chain, they preferably retain fungicidal activity.

Exemplary compounds suitable for reaction with amino piperazine esters of the invention to form polymers include alkylene oxides such as ethylene oxide, propylene oxide, and the like; epihalohydrins such as epichlorohydrin and the like; polycarboxylic anhydrides such as terephthalic anhydride; polycarboxylic acid chlorides such as terephthalic chloride; polyisocyanates such as toluene diisocyanate, diphenylmethane diisocyanate, polymethylene polyphenylene diisocyanate; and mixtures of monomers such as alkylene oxides and alkylene carbonates and the like. Those skilled in the art are familiar with suitable reaction conditions, catalysts and the like and are able to form polymers using the amino piperazine esters of the invention without undue experimentation.

The following examples further illustrate the invention, but are not to be construed as limitations in the scope thereof contemplated herein.

EXAMPLE I: PREPARATION OF AN AMINO PIPERAZINE ESTER

Six moles (775.26 grams) of N-(2-aminoethyl) piperazine having a purity of about 98 percent are added into a three liter reaction flask equipped with a mechanical stirrer, a thermometer, a heat lamp, a temperature controller, and a water cooled condenser. Twelve moles (1056.72 grams) of ethylene carbonate having a purity of about 98 percent are placed in an addition funnel and attached to the reaction flask. A controlled heat lamp is used to keep the contents of the funnel at about 35° to 40° C. to prevent the solidification of the ethylene carbonate. The ethylene carbonate is then added to the N-(2-aminoethyl) piperazine at a rate of about one to three drops per second over an approximately seven hour period with stirring.

The temperature of the contents of the flask increases to about 74° C. and falls to about 68° C. After these temperature changes, the temperature controller is adjusted to maintain the contents at 75° C. for about 1.4 hours, during which the reaction is followed by sampling the flask contents for analysis by liquid chromatography.

A 0.1 gram portion of each sample is dissolved to form a 10% by weight aqueous solution in a mixture of 15% by weight methanol and 85% by weight 0.1 molar aqueous ammonium acetate. The dissolved sample is chromatographed using a column of Partisil ™ PXS 5/25 ODS commercially available from Whatman chemical Separation, Inc. The relative areas of peaks from the chromatograph are assumed to be approximately equal to relative weights of materials analyzed. The final chromatogram indicates that 93.2% of the crude product is 4-[2-(2-hydroxy-1-ethoxycarboxyamino)ethyl]-1-piperazine-carboxylic acid, 1,2-ethanediol monoester, 3.7% is monohydroxyethyl/carbonate material, 2.5% is residual ethylene carbonate and 0.5% is residual N-(2-aminoethyl) piperazine.

Analysis by infrared spectroscopy indicates that substituted piperazine rings, hydroxyl groups and ring nitrogen adjacent to carbonyl are in the product.

EXAMPLE 2: USE OF AN AMINO PIPERAZINE ESTER AS A FUNGICIDE

One milliliter of an 0.1% by weight aqueous solution of the 4-[2-(2-hydroxy-1-ethoxycarboxyamino)ethyl]-1-piperazine-carboxylic acid, 1,2-ethanediol monoester formed in Example I is added to a tube containing eight milliliters of Letheen nutrient broth to form a mixture. Then, one milliliter of an aspergillus niger spore suspension is added to that mixture and mixed by a vortex mixer. The final concentration of the new compound is, therefore, 100 parts per million (ppm). The mixture is allowed to sit at room temperature for 15 minutes. Then, the mixture is again mixed. Triplicate specimens are prepared by spreading one milliliter of the mixture on each of three petri dishes containing plate count agar.

A control sample is prepared by mixing one milliliter of the aspergillus niger spore suspension with nine milliliters of Letheen broth. The mixture is allowed to sit at room temperature for 15 minutes, then mixed again. Triplicate specimens are prepared by spreading one milliliter of the mixture on each of three petri dishes containing plate count agar.

All six petri dishes are placed in a microbiological incubator at 34° C. for five days. After that period, the three control petri dishes are covered with black aspergillus niger growth. The three plates prepared from the mixture containing the compound prepared in Example I have no sign of aspergillus niger growth.

EXAMPLE 3 PREPARATION OF A POLYMER USING AN AMINO PIPERAZINE ESTER

Epoxy resins are prepared using the amounts of the amino piperazine ester product (abbreviated APE) of Example 1 indicated in Table I. Samples of the indicated weight of the esters are measured into glass containers. To each container is added 27.85 g (0.1538 epoxy equivalents) of diglycidyl ether of bisphenol A, having an epoxy equivalent weight of from about 176 to about 183, commercially available from The Dow Chemical Company under the trade designation DER ® 383, and 6.15 g (0.1538 amine active hydrogen equivalents) of an ethylenediamine capped diglycidyl ether of bisphenol A, having an epoxy equivalent weight of from about 182 to about 190, commercially available from The Dow Chemical Company under the trade designation DEH ® 52. Contents of the containers are stirred well by hand. Then portions of the contents of each container are poured onto steel panels, each measuring 4×12 inches, and are smoothed using a draw down rod, which is a rod tightly wrapped with a single layer of wire such that when it is drawn across the viscous resin, a thin layer of relatively even thickness is formed. The weight of resin on each panel is indicated in Table I.

The panels are placed in an oven and maintained at 70° C. for 2 hours, then removed from the oven and left overnight at ambient temperatures. The panels each have a solid coating which is not tacky.

| Example | grams APE | ppm APE | grams on panel |
|---------|-----------|---------|----------------|
| 3.1 | 0.0034 | 100 | 3.5 |
| 3.2 | 0.0069 | 203 | 5.0 |
| 3.3 | 0.0109 | 321 | 3.3 |
| 3.4 | 0.0152 | 447 | 3.4 |
| A* | 0 | 0 | 4.3 |

*Not an example of this invention

Although the invention is described with respect to specific embodiments and modifications, the details hereof are not to be construed as limitations of the invention.

What is claimed is:

1. A compound represented by the formula:

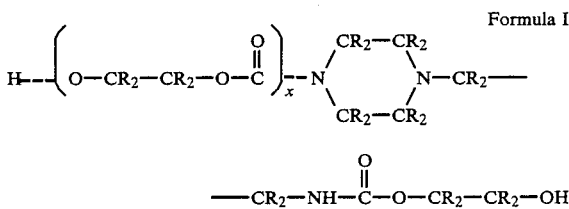

Formula I wherein x is 0 or 1 and each R is independently hydrogen or inert substitution.

2. The compounds of claim 1 wherein each R is independently hydrogen, a nitro group, chlorine, fluorine, bromine, iodine or an alkyl, alkoxy, cycloalkyl, cycloalkoxy, phenoxy or benzyloxy group, wherein the alkyl, cycloalkyl and alkoxy, phenoxy and benzyloxy groups are unsubstituted or inertly substituted.

3. The compounds of claim 2 wherein each R is independently hydrogen, chlorine or an alkyl, alkoxy, cycloalkyl, cycloalkoxy, phenoxy or benzyloxy group, wherein the alkyl, cycloalkyl and alkoxy groups are usubstituted or halogen-substituted and have from 1 to 20 carbons and the phenoxy and benzyloxy groups are unsubstituted or halogen-substituted and have from 6 to 15 carbon atoms.

4. The compound of claim 3 wherein the compound is 4-[2-(2-hydroxy-1-ethoxycarboxyamino)ethyl]-1-piperazine-carboxylic acid, 1,2-ethanediol monoester.

5. A method of retarding or eliminating the growth of a fungus in an environment that is conducive to the growth of the fungus, comprising placing in the environment a growth inhibiting amount of compound having the following formula:

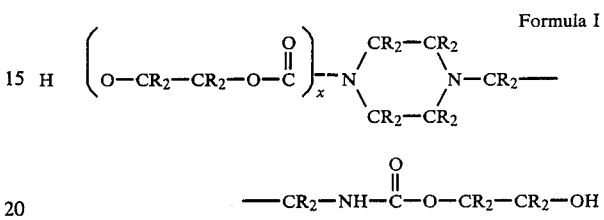

Formula I wherein x is 0 or 1 and each R is independently hydrogen or inert substitution.

6. The method of claim 5 wherein each R is independently hydrogen, a nitro group, chlorine, fluorine, bromine, iodine or an alkyl, alkoxy, cycloalkyl, cycloalkoxy, phenoxy or benzyloxy group, wherein the alkyl, cycloalkyl and alkoxy, phenoxy and benzyloxy groups are unsubstituted or inertly substituted.

7. The method of claim 6 wherein each R is independently hydrogen, chlorine or an alkyl, alkoxy, cycloalkyl, cycloalkoxy, phenoxy or benzyloxy group, wherein the alkyl, cycloalkyl and alkoxy groups are usubstituted or halogen-substituted and have from 1 to 20 carbons and the phenoxy and benzyloxy groups are unsubstituted or halogen-substituted and have from 6 to 15 carbon atoms.

8. The method of claim 7 wherein the 4-[2-(2-hydroxy-1-alkoxycarboxyamino)alkyl]-1-piperazine-carboxylic acid, 1,2-alkanediol monoester is 4-[2-(2-hydroxy-1-ethoxycarboxyamino)ethyl]-1-piperazine-carboxylic acid, 1,2-ethanediol monoester.

9. The method of claim 5 wherein the fungus is aspergillus niger.

* * * * *